(12) United States Patent
Kay

(10) Patent No.: US 6,213,354 B1
(45) Date of Patent: Apr. 10, 2001

(54) SYSTEM AND METHOD FOR DISPENSING FLUID DROPLETS OF KNOWN VOLUME AND GENERATING VERY LOW FLUID FLOW RATES

(75) Inventor: Robert L. Kay, Thousand Oaks, CA (US)

(73) Assignee: Elite Engineering Corporation, Newbury Park, CA (US)

( * ) Notice: Subject to any disclaimer, the term of this patent is extended or adjusted under 35 U.S.C. 154(b) by 0 days.

(21) Appl. No.: 09/474,559

(22) Filed: Dec. 29, 1999

(51) Int. Cl.$^7$ ........................................ B05D 1/00
(52) U.S. Cl. .............................. 222/420; 222/14; 222/55
(58) Field of Search ................................ 222/420–422, 222/1, 14, 52, 55

(56) References Cited

U.S. PATENT DOCUMENTS

| | | | |
|---|---|---|---|
| 3,661,304 | * 5/1972 | Martinez et al. | 222/420 |
| 3,994,423 | * 11/1976 | Burg | 222/420 |
| 4,328,801 | 5/1982 | Marx et al. | 128/214 E |
| 4,432,761 | * 2/1984 | Dawe | 222/420 |
| 4,441,532 | * 4/1984 | Hrubesh | 222/420 |
| 4,643,854 | * 2/1987 | Kendall, Jr. et al. | 222/420 |
| 4,820,281 | 4/1989 | Lawler, Jr. | 604/253 |
| 4,935,261 | 6/1990 | Srivastava et al. | 427/10 |
| 4,936,828 | 6/1990 | Chiang | 604/65 |
| 5,186,057 | 2/1993 | Everhart | 73/861.41 |
| 5,499,545 | * 3/1996 | Kimura et al. | 222/55 |
| 5,588,963 | 12/1996 | Roelofs | 604/65 |
| 5,736,195 | * 4/1998 | Haaland | 427/180 |
| 6,079,283 | * 6/2000 | Papen et al. | 73/864.11 |

* cited by examiner

Primary Examiner—J. Casimer Jacyna
(74) Attorney, Agent, or Firm—Koppel & Jacobs

(57) ABSTRACT

A system and method for dispensing fluid droplets of a known volume uses a control system using inner and outer control loops. The inner control loop includes a pump which pressurizes a fluid against an aperture, causing fluid to pass through the aperture and to a dispensing tip at a particular flow rate. The pressure of the fluid upstream of the aperture is measured and fed back to a controller, which also receives a setpoint input representative of desired dispensed volume. The outer control loop uses a droplet volume measuring system which determines the volume of the droplet that forms at the outlet of the dispensing tip as a result of the applied pressure, the value of which is also fed to the controller. The controller is arranged to maintain the pressure against the aperture (using the inner control loop) as needed to produce a flow rate which will quickly produce a droplet of the desired volume (as determined using the outer control loop), at which time the pressure is reduced to zero and the droplet dispensed

35 Claims, 5 Drawing Sheets

SYSTEM AND METHOD FOR DISPENSING FLUID DROPLETS OF KNOWN VOLUME AND GENERATING VERY LOW FLUID FLOW RATES

BACKGROUND OF THE INVENTION

1. Field of the Invention

This invention is concerned with systems and methods of dispensing precise volumes of fluid in droplet form and of generating very low fluid flow rates.

2. Description of the Related Art

The need to dispense very small volumes of fluid, or to control very low fluid flow rates, routinely arises in chemical and biomedical laboratories, among other places. For example, a type of blood test may require that 5 μL of a blood sample be precisely dispensed onto a slide or plate, or an intravenous medication may need to be provided at a rate expressed in terms of nanoliters or picoliters per second.

Conventionally, such low flow rates and/or dispensed volumes have been provided using a syringe pump to displace a known volume of liquid, and then to provide tubing and/or a needle to route the displaced fluid to its intended destination. This method assumes that the volume displaced by the pump is accurately delivered to the dispensing end of the system. Unfortunately, as the volumes to be controlled become smaller and smaller, significant errors are produced by, for example, the compliance of the tubing, fluids which cling to the needle tip, temperature variations, and inaccuracies in the syringe itself. When the volume needed for a particular purpose can be contained in a single fluid droplet, the accuracy obtainable with such a conventional system is often inadequate.

SUMMARY OF THE INVENTION

A system and method for dispensing fluid droplets of a known volume and for generating very low fluid flow rates is presented which overcomes the problems noted above.

A precisely-controlled fluid flow rate is created using a closed-loop control system. A pump pressurizes a fluid within a piece of tubing against an aperture having a known size, causing fluid to pass through the aperture and out a dispensing tip at a flow rate that varies with the applied pressure. The pressure of the fluid upstream of the aperture is measured and fed to a controller, which also receives a setpoint input representative of desired flow rate. The controller is arranged to control the operation of the pump to maintain the fluid pressure against the aperture as needed to obtain the desired flow rate.

To dispense a fluid droplet having a particular volume, the flow rate loop described above is used as an inner control loop. An outer control loop is formed using a droplet volume measuring system capable of determining the volume of the droplet that forms at the outlet of the dispensing tip as a result of the controlled flow rate. The droplet volume measurement is fed to the controller, along with the measurement of pressure against the aperture and a setpoint representative of the desired dispensed volume. The controller is arranged to maintain the pressure against the aperture (using the inner control loop) as needed to produce a flow rate which will quickly produce a droplet of the desired volume (as determined using the outer control loop), at which time the pressure is reduced to zero. Because the droplet volume is measured at the dispensing tip outlet, all errors introduced along the dispensing path are compensated for. Furthermore, using a controlled flow rate to produce a desired dispensed volume eliminates the need to provide a pump that can control volumetric displacement with great accuracy.

Two methods of measuring droplet volume are described. Under one approach, an imaging system is trained on the forming droplet, with its output provided to a processor. With the focal length of the imaging system known, the processor determines the volume of the nearly symmetric droplet based on its two-dimensional image. A second approach to measuring droplet volume employs a dispensing tip that bends as the forming droplet grows. A laser beam is reflected off the bending tip and onto a position sensitive detector (PSD). The spring rate of the tip and the density of the dispensed fluid are determined in advance, such that the position of the reflected beam provides a measure of the mass of the droplet. The volume of the droplet is then calculated based on its mass.

The invention further contemplates a complete system in which the dispensing tip is moved into a container such as a blood vial from which a sample of fluid is withdrawn, the tip removed from the container and moved into position over a receptacle, and a precise volume of the withdrawn fluid dispensed into the receptacle.

Further features and advantages of the invention will be apparent to those skilled in the art from the following detailed description, taken together with the accompanying drawings.

DETAILED DESCRIPTION OF THE INVENTION

Figure 1:
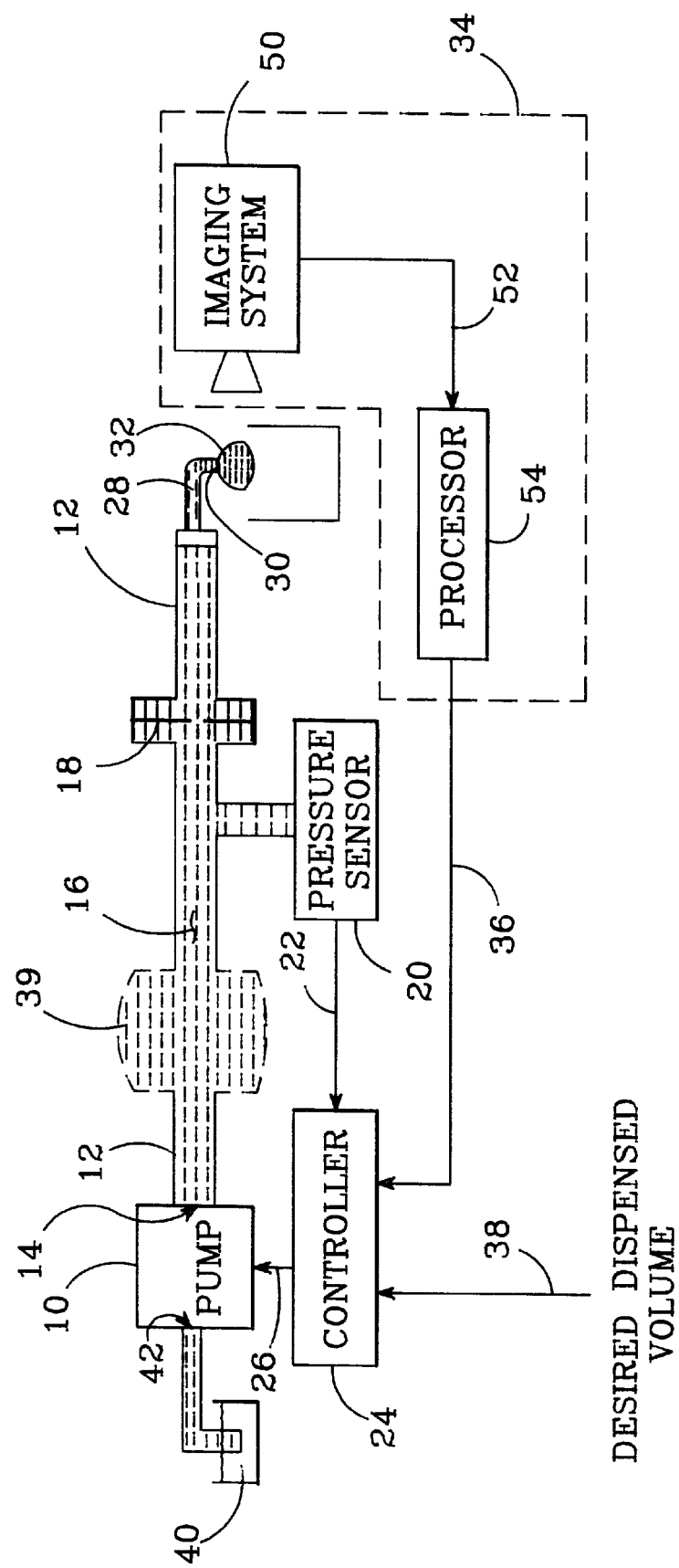
FIG. 1 is a diagram illustrating a system for dispensing fluid droplets of a known volume per the present invention.

A system for dispensing fluid droplets of a known volume is shown in FIG. 1. The system includes a pump 10 having tubing 12 connected to its outlet 14; tubing 12 contains a fluid 16. Downstream of pump 10 is an aperture 18 of a precisely-known size. A pressure sensor 20 is connected to measure the pressure of fluid 16 against aperture 18, and to produce an output signal 22 representative of the measured pressure. Pressure signal 22 is provided to a controller 24, which produces a command signal 26 that controls the operation of pump 10.

Additional tubing 12 leads from the downstream side of aperture 18 to a dispensing tip 28. Fluid 16 that passes through aperture 18 in response to the pressure applied to it by pump 10 eventually appears at the outlet 30 of dispensing tip 28. Outlet 30 is made small enough such that fluid moving at a very low flow rate through the tip initially forms a droplet 32 at the outlet. A droplet volume measurement system 34 is employed to determine the volume of forming droplet 32. System 34 produces an output 36 representative of droplet volume, which is provided as an input to controller 24. Controller 24 also receives a setpoint input 38 representative of the volume of fluid to be dispensed.

Pump 10, aperture 18, pressure sensor 20 and controller 24 form an "inner" control loop, closed around the pressure against aperture 18. In addition, pump 10, droplet volume measuring system 34 and controller 24 form an "outer" control loop, closed around droplet volume. In operation, a desired dispensed volume setpoint 38 is input to controller 24. The controller responds by commanding the pump to produce the pressure against aperture 18 necessary to generate a particular flow rate downstream of aperture 18. The fluid which travels through aperture 18 and tip 28 to tip outlet 30 begins to form a droplet 32. The volume of the growing droplet is monitored by droplet volume measuring system 34, which provides the volume measurement to the controller. The controller is arranged to permit the outer (droplet volume) loop to control the inner (pressure) loop to actively and quickly increase or decrease the size of the forming droplet until it is of the desired size and ready to be dispensed. Because of the very low flow rates needed to form droplets of a desired volume, aperture 18 must be very small, such as might be provided by a pinhole, a nucleated membrane, or a ceramic filter.

It is possible to provide a droplet dispensing system without the use of the invention's inner control loop. A low, fixed flow rate could be established "open loop", i.e., without benefit of a closed control loop which varies pressure (and thus flow rate) in response to measured volume. Using only the outer control loop, fluid would be allowed to flow at the fixed flow rate until a droplet of the desired volume was formed, at which point the pump would be stopped. However, this approach is extremely inefficient when the system is needed to dispense droplets of various sizes. If, for example, a system must dispense droplets of between 2 and 50 $\mu L$, a fixed flow rate of perhaps 1 $\mu L$/sec would be needed to accurately dispense a droplet of 2 $\mu L$, which would require 2 seconds. However, a 50 $\mu L$ drop requires 50 seconds at 1 $\mu L$/sec. In many applications, it is necessary to dispense hundreds of droplets of varying volumes every hour; in such a case, a fixed flow rate may produce droplets at a rate that is unacceptably slow.

The invention avoids this problem with the use of inner and outer control loops. When so arranged, a request for a 2 $\mu L$ droplet results in the controller commanding a very low pressure, resulting in a flow rate that is low enough to enable the small droplet to be accurately formed. Correspondingly, a request for a larger droplet results in a higher pressure and flow rate, so that the larger droplet can be quickly formed. In this way, the system ensures that any desired dispensed volume within the system's capabilities is dispensed quickly and efficiently.

The system preferably includes a flexible cavity 39, which expands as the pressure applied by pump 10 increases. The flexible cavity 39 allows the volume of the fluid upstream of aperture 18 to change while maintaining a constant pressure against aperture 18. A flexible cavity 39 also tends to smooth out pressure variations caused by, for example, types of pumps which lack smooth displacement, temperature variations, or by compliance in the tubing, and to provide a measure of safety by expanding under higher flow conditions.

The described system can be used strictly as a dispensing system, such as might be used to dispense precise volumes of medicines intravenously, in which case the fluid to be dispensed 40 is provided to the inlet 42 of the pump 10. Alternatively, the system can be used as a withdrawal and dispensing system (described in detail below), in which fluid is both drawn into and dispensed from the dispensing tip. In either case, pump 10 is preferably bi-directional; i.e., capable of providing either a positive pressure or a negative pressure against aperture 18. A bi-directional pump allows the control loops to increase (by applying positive pressure) or decrease (by applying negative pressure) the volume of a forming droplet as needed to obtain a desired volume. A bi-directional pump is essential when the system is used as a withdrawal and dispensing system, so that fluid may be drawn into the dispensing tip.

Two droplet measurement systems 34 are described herein; one of these is shown in FIG. 1. An imaging system 50 such as a camera is aimed at the dispensing tip outlet 30 to observe the formation of droplet 32. The focal length between the camera and the tip outlet is determined in advance, as is the camera-to-drop magnification, enabling a size-per-pixel correspondence to be established; these parameters are provided to a processor 54 connected to receive the output 52 of imaging system 50. With a known size-per-pixel factor and a symmetrical droplet, the processor analyzes the droplet image to determine how many pixels (and thus how many microns) across the droplet is at its widest point. From this, the processor can calculate the volume of the drop, which it provides to controller 24 as signal 36. Tip outlet 30 should be symmetrical to produce symmetrical droplets.

Figure 2:
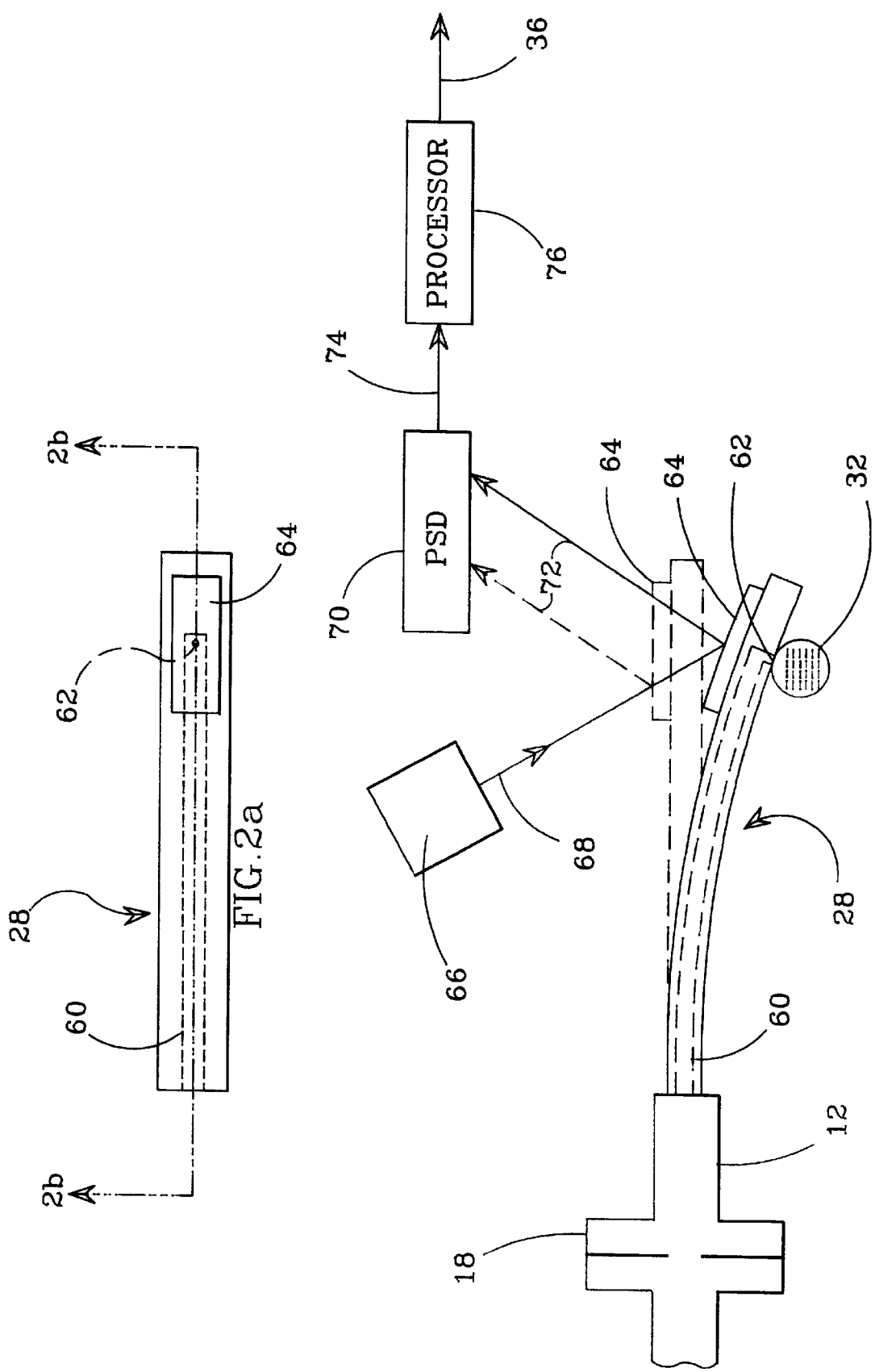
FIGS. 2a and 2b are diagrams illustrating plan and corresponding cross-sectional views, respectively, of a droplet volume measuring system per the present invention.

An alternative droplet volume measuring system 34 which uses a gravimetric method to measure droplet volume is illustrated in FIGS. 2a and 2b. FIG. 2a is a plan view of an embodiment of dispensing tip 28, with a corresponding cross-sectional view of tip 28 shown in FIG. 2b. A channel 60 runs through tip 28 and terminates at a small aperture 62, such that fluid introduced at one end of channel 60 is conveyed by the channel to the aperture. As fluid slowly passes through the aperture, it begins to form into a droplet 32. The end of dispensing tip 28 opposite aperture 62 is rigidly attached to tubing 12 downstream of aperture 18, with the rest of tip 28 unsupported and extending freely and approximately horizontally from tubing 12. Tip 28 is intentionally made flexible, so that as a droplet forms, the aperture end of the tip progressively droops lower and lower as the weight of the droplet increases. The spring rate of the tip, i.e., a quantity that defines the distance that the aperture end moves for a given weight, is determined in advance of using the measuring system 34, with the length, width, thickness and material of tip 28 selected to allow flexure to occur with extremely small volume droplets formed around aperture 62.

A reflective area 64 is placed on the side of tip 28 opposite aperture 62, which droops with the tip as the mass of forming droplet 32 increases. A laser 66 is positioned such that its beam 68 strikes the reflective area 64 at a first angle with respect to the plane of the tip. The first angle should be selected such that the beam strikes the reflective area in any of the tip's expected positions. A position sensitive detector (PSD) 70 is positioned to detect the position of the beam after it has been reflected. The position of the reflected beam 72 varies depending on the deflection of tip 28, which varies with the mass of the forming droplet 32; the PSD outputs a signal 74 representing the reflected beam's position to a processor 76. The density of the droplet's fluid is determined in advance. With droplet density and mass known, the processor 76 calculates the droplet's volume, which it outputs as a signal 36 to the controller 24.

Channel 60 in tip 28 may be an open or a closed channel. If open, channel 60 should be narrow enough to enable fluid to be conveyed via surface tension. If fluid is to be withdrawn as well as dispensed with tip 28, the channel is preferably closed, so that a negative pressure at aperture 18 will cause fluid to be drawn up the tip.

The presence of reflective area 64 may also enable some type of vision system to determine the location of the droplet in the X-Y plane in which the tip lies. This droplet location information can be used if the tip is to be moved to a target location where the formed droplet is to be dispensed (discussed in detail below).

Each of the described droplet measuring systems has advantages and disadvantages. The droplet measuring system of FIGS. 2a and 2b may provide more accuracy than that shown in FIG. 1, but it requires that the density of the dispensed fluid be known. Density is irrelevant to the FIG. 1 system, but it may be difficult to obtain an accurate volume measurement for very small droplets. As noted above, an imaging system such as that shown in FIG. 1 determines the width of a droplet in pixels. If the droplet and magnification is such that a considerable number of pixels (>20) fit across the droplet, a fairly precise determination of droplet size can be made. If only a small number of pixels fit within across the droplet image, however, accuracy will be degraded. The droplet measuring system shown in FIG. 1 also tends to require complex software and expensive hardware to perform well enough to be part of a control loop closed on droplet size. The invention is not limited to these two approaches; many other droplet volume measurement techniques might be employed.

Figure 3:
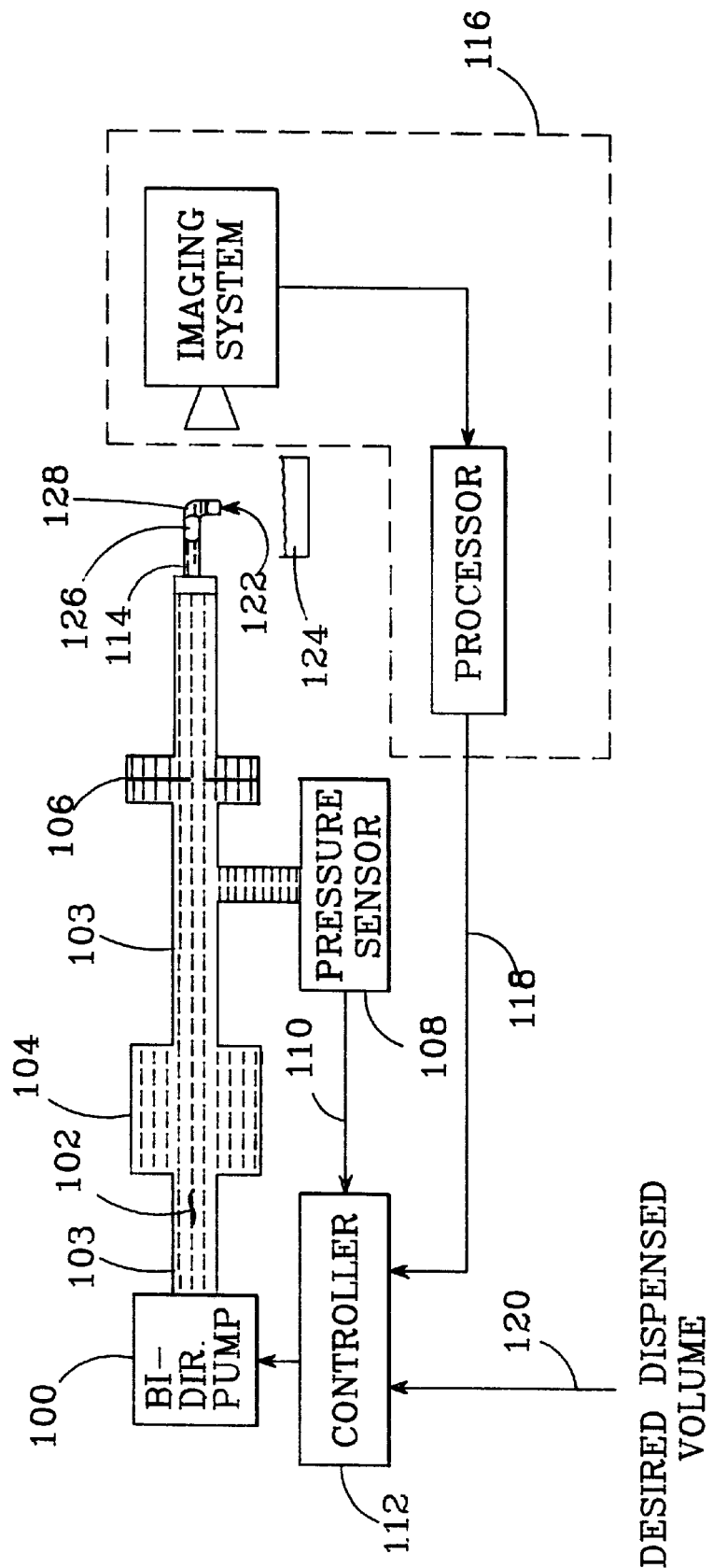
FIG. 3 is a diagram illustrating a system for withdrawing and dispensing fluid droplets of a known volume per the present invention.

A system for withdrawing fluid and dispensing a droplet of the withdrawn fluid is shown in FIG. 3. The system is essentially identical to that shown in FIG. 1, including a pump 100 which pressurizes a fluid 102 through tubing 103 and a flexible cavity 104 against a precision aperture 106. A pressure sensor 108 outputs a signal 110 to a controller 112 that represents the pressure against aperture 106, with controller 112 controlling the operation of pump 100. A dispensing tip 114 is connected to tubing 103 downstream of aperture 106, and a droplet volume measuring system 116 provides an output 118 to controller 112 representing the volume of a droplet.

Because such a system must withdraw as well as dispense fluid, pump 100 must be bi-directional, so that both positive and negative pressures may be applied against aperture 106. In a basic mode of operation, a desired dispensed volume input 120 is provided to controller 112. The outlet 122 of dispensing tip 114 is immersed into a fluid 124 to be dispensed, and controller 112 commands a negative pressure. This causes a quantity of fluid to be drawn into tip 114. A droplet of the desired volume is then formed at the outlet 122 of tip 114 as described above.

The fluid 102 within tubing 103 and the fluid 124 drawn into tip 114 may be the same fluid. However, it may be preferable that the two fluids be different. If fluid 102 is always the same, its density and other characteristics will be well-known and the system can be optimized for this fluid. Water is an example of a fluid that would serve well as fluid 102, as its characteristics are well-known and it should not unduly degrade the system components. However, when the two fluids are different, it is important that they not come into contact, so that neither fluid becomes contaminated by the other. Operation of the system when using two different fluids is illustrated in FIG. 3. Prior to drawing any of fluid 124 into dispensing tip 114, a negative pressure is briefly applied against aperture 106 to draw a small amount of air 126 into the tip. This bolus of air 126 provides a barrier between fluid 102 and fluid 124. The tip outlet 122 is then lowered into fluid 124 and negative pressure again applied, thereby drawing a sample 128 of fluid 124 into the tip.

When the volume to be dispensed to very small, one more brief application of negative pressure may be advisable after drawing sample 128 into tip 114. This is to ensure that the sample fluid is clear of outlet 122, eliminating a possible source of error when a droplet is dispensed. It may also be advisable to dip the tip outlet 122 into a cleaning solution after fluid 124 has been drawn in, so that the outlet is clear when it is time to dispense a droplet. Such a cleaning step is also recommended after a droplet has been dispensed, particularly when individual biomedical samples are being sequentially withdrawn and dispensed.

With the fluid sample 128 drawn into tip 114, the controller 112 commands a positive pressure as necessary to cause a droplet of the desired volume to form on outlet 122, at which point the pressure is reduced to zero. The formed droplet is then dispensed, preferably by touching it to its target—referred to as "touching off" the droplet; once the droplet contacts its target, surface tension causes the droplet to remain on the target.

A small quantity of fluid may remain on the tip after the droplet has been touched off. However, this quantity will be fairly constant from droplet to droplet, and its volume can be determined empirically in advance. This volume value is provided to the controller, which causes the size of the droplet to be increased accordingly, so that the touched-off volume is nearly equal to the desired dispensed volume.

Figure 4:
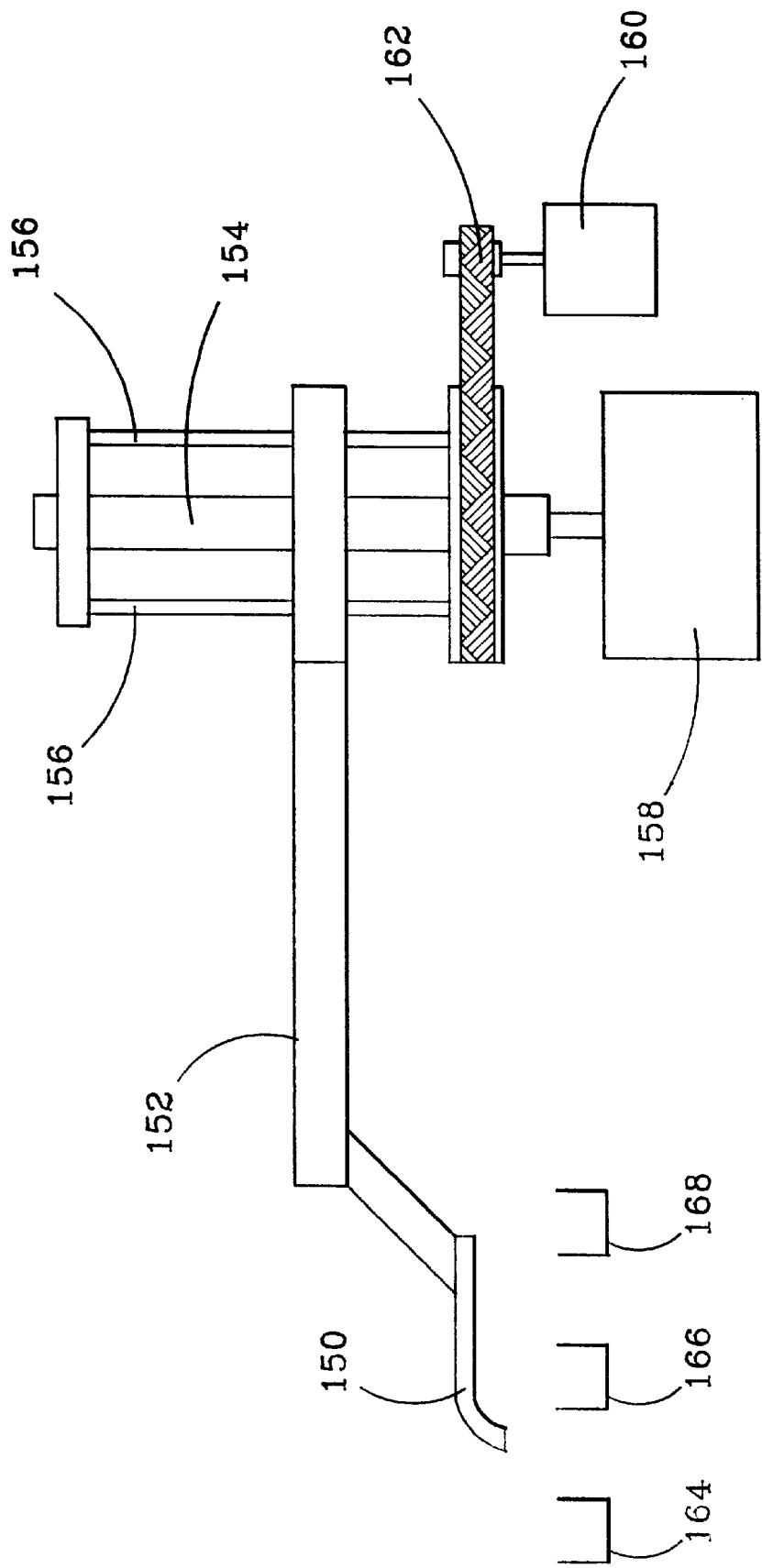
FIG. 4 is a diagram illustrating a mechanism usable for moving the dispensing tip of a system for withdrawing and dispensing fluid droplets of a known volume per the present invention.

In a typical application, it is necessary that the dispensing tip of the present invention be capable of movement, particularly in system that both withdraw and dispense fluid. As noted above, for each dispensed droplet, the tip may need to be lowered into a container of the fluid to be dispensed, moved over and lowered into a cleaning solution, moved over a target and lowered to touch off a droplet of the desired volume, and again moved over and lowered into a cleaning solution. Numerous mechanisms could be employed for this purpose, one example of which is shown in FIG. 4. Here, a dispensing tip 150 is mounted onto a support bar 152, which is attached to a structure that can raise and lower the support bar, as well as move the bar in a circular arc around the mechanism. The support bar 152 is attached to a Z-axis actuator 154, which is driven up and down on guiderails 156 by a motor 158, via a lead screw arrangement, for example. The support bar 152 traces an arc via a motor 160, which rotates the Z-axis actuator around a pivot axis using a belt 162. Such a mechanism can guide dispensing tip 150 into, for example, a cleaning solution container 164, a vial of fluid to be dispensed 166, and a target container 168, assuming the various containers are all within the range of the mechanism. Many other possible mechanisms could be employed to move the dispensing tip as needed, some having additional degrees of freedom; the mechanism in FIG. 4 is merely illustrative.

Figure 5:
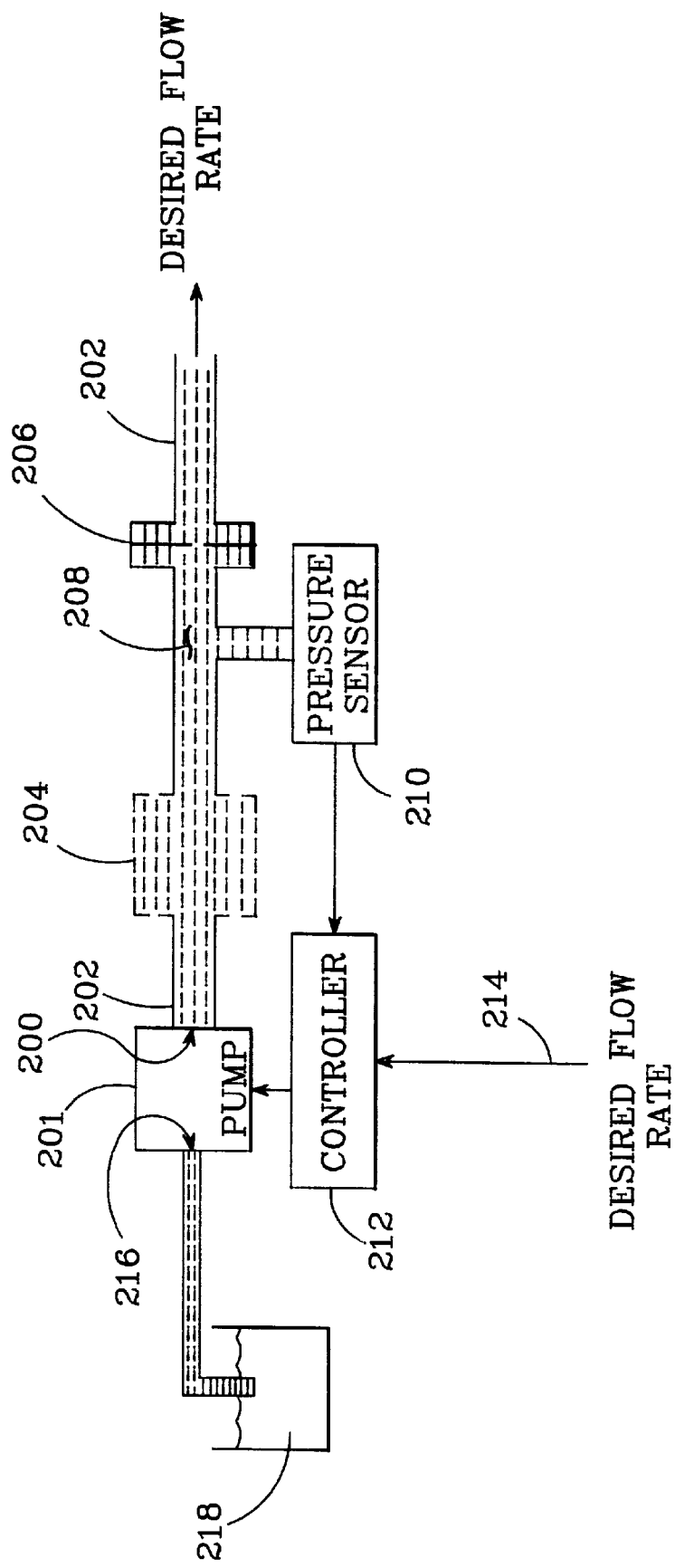
FIG. 5 is a diagram illustrating a system for providing very low fluid flow rates per the present invention.

The inner loop of the droplet dispensing system described above may be used in a standalone manner as a system for generating very fluid low flow rates. Such a system is illustrated in FIG. 5. The outlet 200 of a pump 201 is connected to tubing 202, which is preferably connected to a flexible cavity 204 and a precision aperture 206. A fluid 208 to be conveyed at a desired flow rate is contained within tubing 202, and a pressure sensor 210 is connected to measure the pressure of the fluid against aperture 206. Pressure sensor 210 provides an output representative of the measured pressure to a controller 212, which also receives a setpoint input 214 representative of the desired flow rate. Downstream of aperture 206, tubing 202 may be connected to a dispensing tip or to additional plumbing (not shown) which conveys fluid 208 where needed. When a continuous flow rate is to be maintained, an inlet 216 of pump 201 may be plumbed to a source 218 of fluid 208.

In operation, a desired flow rate setpoint is provided to controller 212, which commands pump 201 to pressurize fluid 208 against aperture 206 as necessary to obtain the desired flow rate downstream of the aperture. Pump 201, pressure sensor 210 and controller 212 form a control loop closed around the measured pressure, which ensures that the desired flow rate will be maintained. To obtain the very low flow rates for which this arrangement is best suited, aperture 206 need be very small, such as might be provided by a pinhole, a nucleated membrane, or a ceramic filter.

The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

I claim:

1. A low volume fluid droplet dispensing system, comprising:
    a pump which provides a fluid at a pump outlet in response to a control signal,
    tubing connected to the outlet of said pump,
    an aperture in said tubing downstream of said pump, said fluid pressurized against said aperture by said pump and passing through said aperture at a flow rate which varies with the magnitude of the pressure applied by said pump on said fluid,
    a pressure sensor which provides an output signal representative of the pressure of said fluid against said aperture,
    a controller connected to receive a setpoint signal representative of a desired dispensed volume, said pressure sensor output signal, and a signal representative of dispensed fluid volume as inputs, and to produce said control signal to said pump as an output,
    a dispensing tip on said tubing downstream of said aperture, and
    a droplet volume measuring means arranged to measure the volume of a droplet that forms at the outlet of said dispensing tip, said droplet volume measuring means providing said signal representative of dispensed fluid volume to said controller, said pump, pressure sensor, and controller forming an inner control loop closed around the pressure against said aperture and said pump, droplet volume measuring means, and controller forming an outer control loop closed around droplet volume, said controller arranged to vary the pressure against said aperture to produce a droplet at said dispensing tip outlet having the desired dispensed volume.

2. The system of claim 1, wherein said pump is a syringe.

3. The system of claim 1, wherein said droplet volume measuring means comprises an imaging system and a processor, said imaging system arranged to produce a signal representative of an image of said droplet to said processor, said processor programmed to compute the volume of said drop based on said image signal and to output a signal representative of said volume to said controller.

4. The system of claim 3, wherein said imaging system comprises a camera.

5. The system of claim 1, wherein said dispensing tip bends in response to the weight of said droplet, said tip having a predetermined spring rate and said droplet having a predetermined density, said droplet volume measuring means comprising:
    a reflective area on said tip which moves with said tip in response to the weight of said droplet,
    a laser beam directed onto said reflective area,
    a position sensitive detector (PSD) arranged to receive said reflected beam from said reflective area and to output a signal representative of the position of said beam, and
    a processor arranged to determine the volume of said droplet based on said PSD output, said predetermined spring rate, and said predetermined density, and to output a signal representative of said volume to said controller.

6. The system of claim 1, wherein said aperture comprises a pinhole.

7. The system of claim 1, wherein said aperture comprises a nucleated membrane.

8. The system of claim 1, wherein said aperture comprises a ceramic filter.

9. The system of claim 1, further comprising a flexible cavity in said tubing between said pump and said aperture which acts to maintain said pressure within said tubing nearly constant for a changing volume of fluid in said tubing.

10. The system of claim 1, wherein said pump is a bi-directional pump such that the volume of said droplet can be increased or decreased.

11. A low volume fluid withdrawal and dispensing system, comprising:
    a bi-directional pump which provides positive or negative pressure at a pump outlet in response to a control signal,
    tubing connected to the outlet of said pump, said tubing at least partially filled with a first fluid,
    an aperture in said tubing downstream of said pump, said first fluid pressurized against said aperture by said pump and passing through said aperture at a flow rate which varies with the magnitude of the pressure applied by said pump on said first fluid,
    a pressure sensor which provides an output signal representative of the pressure of said first fluid against said aperture,
    a controller connected to receive a setpoint signal representative of a desired dispensed volume, said pressure sensor output signal, and a signal representative of dispensed fluid volume as inputs, and to produce said control signal to said pump as an output,
    a withdrawal/dispensing tip on said tubing downstream of said aperture, and
    a droplet volume measuring means arranged to measure the volume of a droplet of a second fluid that forms at the outlet of said withdrawal/dispensing tip, said droplet volume measuring means providing said signal representative of dispensed fluid volume to said controller, said pump, pressure sensor, and controller forming an inner control loop closed around the pressure against said aperture and said pump, droplet volume measuring means, and controller forming an outer control loop closed around droplet volume, said controller arranged to, with said withdrawal/ dispensing tip immersed in a second fluid, command a negative pressure at said pump outlet to withdraw a quantity of said second fluid into said tip, said controller further arranged to vary the pressure against said aperture to produce a droplet of said second fluid at said withdrawal/dispensing tip outlet having the desired dispensed volume.

12. The system of claim 11, wherein said first fluid and said second fluid are the same fluid.

13. The system of claim 11, wherein said first fluid and said second fluid are different fluids.

14. The system of claim 13, wherein said controller is further arranged to command a negative pressure at said pump outlet prior to said tip being immersed in said second fluid to withdraw a quantity of air into said tip so that, when said second fluid is drawn into said tip, a bolus of air is present between said first fluid and said withdrawn second fluid.

15. The system of claim 14, further comprising a means for moving said tip vertically and horizontally.

16. The system of claim 15, wherein said means for moving said tip is programmed to move said tip into and out of a container of said second fluid where said second fluid is withdrawn, and to a target location where said second fluid is dispensed.

17. The system of claim 16, wherein said means for moving said tip is further programmed to, when said droplet of said desired dispensed volume is formed at the outlet of said dispensing tip, lower said tip to a target surface to touch off said droplet.

18. The system of claim 16, wherein said means for moving said tip is further programmed to move said tip into a cleaning solution prior to moving said tip into and out of a container of said second fluid.

19. The system of claim 13, wherein said first fluid is water.

20. The system of claim 11, wherein a predetermined quantity of said second fluid adheres to said tip after said formed droplet is dispensed, said controller arranged to vary the pressure against said aperture to produce a droplet of said second fluid at said withdrawal/dispensing tip outlet having a volume that is greater than the desired dispensed volume by said predetermined quantity to compensate for said adhering fluid.

21. A method of dispensing a droplet of fluid having a desired volume, comprising the steps of:

providing a value representing the desired volume of a fluid droplet to be dispensed, pressurizing a fluid against an aperture of a known size within a length of tubing, measuring the pressure of said fluid against said aperture, conveying the fluid which passes through said first aperture in response to said pressure to a dispensing tip, measuring the volume of a droplet of said fluid as it forms at the outlet of said tip in response to said pressure, computing a pressure value based on said volume measurement and said desired fluid volume value that, when used to pressurize said fluid against said aperture, results in said droplet quickly obtaining said desired volume, adjusting the pressure of said fluid against said aperture to correspond to said computed pressure value, and reducing said pressure on said fluid to zero when said droplet has obtained said desired volume.

22. The method of claim 21, further comprising the step of touching off said droplet to dispense it.

23. The method of claim 21, wherein said step of measuring the volume of said droplet comprises the steps of:

obtaining an image of said droplet, and computing the volume of said droplet based on the size of said imaged droplet.

24. The method of claim 23, wherein said image is obtained with an imaging system which produces an image made up of pixels, further comprising the step of determining a droplet size-per-pixel value for use in determining the size of said droplet from said imaged droplet.

25. The method of claim 21, wherein said step of measuring the volume of said droplet comprises the steps of:

forming said droplet on the end of a dispensing tip which bends in response to the weight of said droplet, said droplet having a predetermined density and said tip having a predetermined spring rate, reflecting a laser beam off of a portion of said dispensing tip which moves as said tip bends in response to the weight of said droplet, detecting the position of said reflected beam, computing the mass of said droplet based on the position of said reflected beam and said predetermined spring rate, and computing the volume of said droplet based on its computed mass and said predetermined density.

26. A method of withdrawing fluid from a container and of dispensing a droplet of said fluid having a desired volume, comprising the steps of:

providing a value representing the desired volume of a droplet of a first fluid to be dispensed, immersing the outlet of a dispensing tip in said first fluid, establishing a negative pressure within a length of tubing connected to said dispensing tip to withdraw a quantity of said first fluid into said tip, removing said tip from said first fluid, pressurizing a second fluid against an aperture within said tubing, measuring the pressure of said second fluid against said aperture, conveying the fluid which passes through said first aperture in response to said pressure toward said dispensing tip via said tubing, thereby applying pressure to said quantity of said first fluid withdrawn into said tip, measuring the volume of a droplet of said first fluid as it forms at the outlet of said tip in response to said pressure, computing a pressure value based on said volume measurement and said desired fluid droplet volume value that, when used to pressurize said second fluid against said aperture, results in said droplet quickly obtaining said desired volume, adjusting the pressure of said second fluid against said aperture to correspond to said computed pressure value, and reducing said pressure on said second fluid to zero when said droplet has obtained said desired volume.

27. The method of claim 26, further comprising the step of touching off said formed droplet to dispense it.

28. The method of claim 27, further comprising the step of moving said tip from a first location near said first fluid to a target location where said droplet is touched off.

29. The method of claim 27, wherein a predetermined quantity of said second fluid adheres to said tip after said formed droplet is dispensed, said step of computing said pressure value further comprising increasing said computed pressure value as needed to compensate for said adhering fluid such that said dispensed volume is about equal to said desired volume.

30. The method of claim 26, further comprising the step of, prior to immersing the outlet of the dispensing tip in said first fluid, establishing a negative pressure within said length of tubing while the outlet of said dispensing tip is open to the atmosphere to withdraw a bolus of air into the tip such that, after said quantity of said first fluid is withdrawn into said tip, said bolus separates said first fluid from said second fluid.

31. The method of claim 26, further comprising the steps of, prior to immersing the outlet of the dispensing tip in said first fluid, immersing said tip in a cleaning solution and removing said tip from said cleaning solution.

32. The method of claim 26, wherein said first fluid and said second fluid are the same fluid.

33. The method of claim 26, wherein said first fluid and said second fluid are different fluids.

34. A fluid droplet dispensing tip and volume measuring system, comprising:
  a channel having first and second ends, said channel having a predetermined spring rate along its length between said first and second ends,
  an aperture formed at said second end of said channel, said channel arranged such that a fluid introduced at said first end is conveyed by said channel to said aperture, said aperture arranged such that fluid conveyed to said aperture by said channel forms into a droplet around said aperture, said channel fixed at said first end and extending freely and approximately horizontally from said fixed end, said predetermined spring rate such that said aperture end progressively droops with respect to said first end as the weight of said droplet increases, said droplet having a predetermined density,
  a reflective area near said aperture that moves with said aperture as the weight of said droplet increases,
  a laser beam directed onto said reflective area,
  a position sensitive detector (PSD) arranged to receive said reflected beam from said reflective area and to output a signal representative of the position of said beam, and
  a processor arranged to determine the volume of said droplet based on said PSD output, said predetermined spring rate, and said predetermined density, and to output a signal representative of said volume.

35. The dispensing tip of claim 34, wherein the diameter of said channel is such that fluid introduced at said first end is conveyed by said channel to said aperture end by surface tension.

* * * * *